(12) United States Patent
Flock et al.

(10) Patent No.: US 6,424,863 B1
(45) Date of Patent: Jul. 23, 2002

(54) DELIVERY OF PHARMACEUTICAL COMPOUNDS AND COLLECTION OF BIOMOLECULES USING ELECTROMAGNETIC ENERGY AND USES THEREOF

(76) Inventors: Stephen T. Flock, 17 Gillards Rd.; Kevin S. Marchitto, 127 Bellbird Rd., both of Mt. Eliza, 3930 VIC (AU)

(*) Notice: Subject to any disclaimer, the term of this patent is extended or adjusted under 35 U.S.C. 154(b) by 0 days.

(21) Appl. No.: 09/535,150

(22) Filed: Mar. 24, 2000

Related U.S. Application Data

(60) Provisional application No. 60/126,296, filed on Mar. 26, 1999, now abandoned.

(51) Int. Cl.⁷ .................................. A61N 1/30
(52) U.S. Cl. .............................. 604/20; 604/21; 604/22
(58) Field of Search .............................. 604/20, 21, 22, 604/500; 606/3, 9, 10, 17

(56) References Cited

U.S. PATENT DOCUMENTS

| 5,643,252 A | 7/1997 | Waner |
| 6,056,738 A | 5/2000 | Marchitto |
| 6,251,102 B1 * | 6/2001 | Gruzdev et al. .............. 372/34 |
| 6,315,772 B1 * | 11/2001 | Marchitto et al. ............ 604/21 |

* cited by examiner

Primary Examiner—Joseph Pelham
Assistant Examiner—Vinod D Patel
(74) Attorney, Agent, or Firm—Benjamin Aaron Adler

(57) ABSTRACT

A method/system to enhance continuous delivery of pharmaceutical compounds in a target by utilizing non-ionizing electromagnetic energy.

24 Claims, No Drawings

DELIVERY OF PHARMACEUTICAL COMPOUNDS AND COLLECTION OF BIOMOLECULES USING ELECTROMAGNETIC ENERGY AND USES THEREOF

CROSS-REFERENCE TO RELATED APPLICATION

This non-provisional patent application claims benefit of provisional patent application U.S. Serial No. 60/126,296, filed Mar. 26, 1999, now abandoned.

BACKGROUND OF THE INVENTION

1. Field of the Invention

The present invention relates generally to the fields of medical physics and drug delivery. More specifically, the present invention relates to a method of continuous delivery of pharmaceutical compounds using electromagnetic energy.

2. Description of the Related Art

Various methods have been used for facilitating the delivery of compounds across the skin and other membranes. Iontophoresis uses an electric current to increase the permeation rate of charged molecules. However, iontophoresis is dependent on charge density of the molecule and has further been known to cause burning in patients. Use of ultrasound has also been tested whereby application of ultrasonic energy to the skin results in a transient alteration of the skin, which leads to an increased permeability to substances. Electromagnetic energy produced by lasers may be used to ablate stratum corneum in order to make the skin more permeable to pharmaceutical substances (U.S. Pat. No. 4,775,361), and impulse transients generated by lasers or by mechanical means may be used to make alterations in epithelial layers that result in improved permeation of compounds (U.S. Pat. No. 5,614,502).

Skin has a very thin layer of dead cells, called the stratum corneum, which acts as an impermeable layer to matter on either side of the layer. The stratum corneum primarily provides the skin's barrier function. If the stratum corneum is removed or somehow altered, materials can more easily diffuse into or out of the skin. Alternatively, compounds referred to as permeation enhancers (e.g. alcohol) or drug carriers (e.g. liposome) can be used, with some success, to penetrate the stratum corneum. In any case, the barrier function of the skin presents a very significant problem to pharmaceutical manufacturers who may be interested in topical administration of drugs, or in cutaneous collection of bodily fluids.

Mucosa, the moist lining of many tubular structures and cavities (e.g. nasal sinuses and mouth), consists in part of an epithelial surface layer. This surface layer consists of sheets of cells in single or multiple layers with strong intercellular bonds, and has a non-keratinized or keratinized epithelium. On the basolateral side of the epithelium is a thin layer of collagen, proteoglycans and glucoproteins called the basal lamina, which serves to bind the epithelial layer to the adjacent cells or matrix. The mucosa acts as a barrier to prevent the significant absorption of topically applied substances, as well as the desorption of biomolecules and substances from within the body. The degree to which mucosa acts as a barrier, and the exact nature of the materials to which the mucosa is impermeable or permeable, depends on the anatomical location. For example, the epithelium of the bladder is 10,000 times less "leaky" to ions than the intestinal epithelium.

The mucosa is substantially different from skin in many ways. For example, mucosa does not have a stratum corneum. Despite this difference, permeation of compounds across mucosa is limited and somewhat selective. The most recent model of the permeability of mucosa is that the adjacent cells in the epithelium are tightly bound by occluding junctions, which inhibit most small molecules from diffusing through the mucosa, while allowing effusion of mucoid proteins. The molecular structure of the epithelium consists of strands of proteins which link together between the cells, as well as focal protein structures such as desmosomes. The permeation characteristics of mucosa are not fully understood, but it is conceivable that the selective permeability of the mucosa may depend on its epithelial layer as well as the basal lamina. While it has been shown that removal or alteration of the stratum corneum of skin can lead to an increase in skin permeability, there is no corresponding layer on the mucosa to modify.

There are methods on transdermal drug delivery enhancements using laser ablation or alteration of stratum corneum. More recent technology involves using shock waves to make stratum corneum and cell walls more permeable. One of the problems with the available methods of drug delivery enhancement is that the tissue is altered transiently to be made permeable. Furthermore, there is little or no control over the degree of tissue alteration, and no control over how much drug is delivered.

The prior art is deficient in the lack of effective means of improving the permeation rates of pharmaceutical compounds across biological membranes, e.g. mucosa and skin. Specifically, the prior art is deficient in the lack of effective means of enhancing drug delivery by utilizing non-ionizing electromagnetic energy. The present invention fulfills this long-standing need and desire in the art.

SUMMARY OF THE INVENTION

The present invention describes methods and apparatus for improving the permeation rates of pharmaceutical compounds across biological membranes. Also provided is a method for increasing the diffusion of substances out of tissue.

The present invention uses electromagnetic energy including radiofrequency energy to create propagating pressure waves. These pressure waves can be used to push the drug molecules into the skin or other membranes, or push biomolecules out of the skin. This method allows for continuous and controllable transmembrane drug delivery. In the presence of propagating pressure waves, molecules in a mobile phase (e.g. the drug) would be pushed in the direction of wave propagation while the static phase (e.g. the tissue) would maintain it's position.

In one embodiment of the present invention, there is provided a method for enhancing continuous delivery of a pharmaceutical compound in a subject, comprising the steps of irradiating the subject with electromagnetic energy continuously; and applying the pharmaceutical compound to the subject. The pharmaceutical compound interacts with the electromagnetic energy. Examples of electromagnetic energy include radiofrequency and microwave. Pharmaceutical compound can be an anesthetic drug, an antineoplastic drug, a photodynamic therapeutical drug or any other drug that can interact with electromagnetic energy and be propelled through subject's barrier.

In another embodiment of the present invention, there is provided a method for increasing diffusion rate of a substance in a medium, comprising the step of applying electromagnetic energy to the medium, wherein the electromagnetic energy generates propagating pressure wave upon the medium. The medium can be a liquid or semi-solid medium.

In still another embodiment of the present invention, there is provided a method for improving permeation rate of a molecule through a barrier, comprising the step of applying electromagnetic energy to the barrier, wherein the electromagnetic energy ablates or alters the structure of the barrier. The barrier can be biological and non-biological. Examples of biological barrier include skin, vaginal wall, uterine wall, intestinal wall, buccal wall, tongue, nasopharyngeal wall, anal wall, bladder wall, vascular vessel, lymphatic vessel and urethral vessel.

In yet another embodiment of the present invention, there is provided a method for creating pores in a barrier thereby improving permeation rate of a molecule through the barrier, comprising the step of applying electromagnetic energy with a probe to the barrier, wherein the probe conducts the electromagnetic energy. Specifically, the probe is made of silicon with a metallic conducting material.

In still yet another embodiment of the present invention, there is provided a method for enhancing continuous delivery of a pharmaceutical compound in a subject, comprising the steps of treating the subject to weaken the barrier function of its membrane first; irradiating the pre-treated subject with electromagnetic energy continuously; and applying the pharmaceutical compound to the subject. The subject can be pre-treated with electromagnetic energy, or using other membrane-weakening method.

Further provided in the present invention is a system for enhancing continuous delivery of a pharmaceutical compound in a subject, comprising a means to generate electromagnetic energy; a means to deliver the electromagnetic energy to the subject continuously; and a means to administer the pharmaceutical compound to the subject. Preferably, the system further comprises a probe which is delivered to the subject at the same time as the electromagnetic energy. Specifically, the probe is made of a magnetic material, such as a metal.

Other and further aspects, features, and advantages of the present invention will be apparent from the following description of the presently preferred embodiments of the invention given for the purpose of disclosure.

DETAILED DESCRIPTION OF THE INVENTION

The present invention discloses methods to make targets associated with tissue interfaces permeable to diagnostic and therapeutic substances. The invention uses non-ionizing electromagnetic energy to increase the diffusion rate of substances into or out of tissues. These methods, referred to as "electromagnetic energy-enhanced delivery", involve the transient or sustained alteration of membranes and tissue interfaces caused by electromagnetic energy including wavelengths much longer than those of light. The electromagnetic energy described herein is often referred to as microwave and radiofrequency.

There are a variety of aspects of continuous delivery of pharmaceutical compounds across membranes using electromagnetic energy. In one aspect, propagating pressure waves are used to create pressure in a medium such that the diffusion rate of the substances in the medium (usually a drug formulation) is increased relative to its surrounding environment. In a related aspect, these pressure waves are used to create transient alterations in the membrane or tissue. Alternatively, a trap is formed which generates a electromagnetic dipole in the tissue. Movement of this trap relative to the substance creates an electromagnetic gradient, which essentially "pulls" the molecules along. Electromagnetic energy used to ablate or alter molecular structures in the skin or mucosa is discussed as a means of "opening" pores to further improve permeation rates of molecules. Electromagnetic energy can also be used to ablate or alter skin or membranes thus reducing their barrier function and providing a way for molecules to diffuse. Some of these aspects might benefit from a molecular alteration of the pharmaceutical being delivered; therefore some specific drug formulations were tried for use in conjunction with electromagnetic energy.

Enhancement of drug delivery can take place with the use of osmotic or atmospheric pressure (applied, for example, in the form of a patch over the site of irradiation). A patch of distilled water in contact with the treated skin would enhance the diffusion of glucose out of the skin due to osmotic pressure. A patch which positions a drug in intimate contact with the skin or mucosa, and has an adjacent chamber with an increased pressure would tend to push the drug into the tissue.

There are many therapeutic and diagnostic procedures that would benefit from a transmucosal or transendothelial route of administration or collection. For example, it is a specific object of the present invention to describe methods and devices for delivery of local anesthetics, such as lidocaine, to a region prior to a medical treatment. Such a local administration of lidocaine could be efficacious at providing anesthesia, but would minimize any side-effects and eliminate the need for a needle. Local administration of an antineoplastic drug into the bladder wall could greatly minimize the time required for a patient to hold a drug in the bladder during chemotherapy.

Electrosurgery, which is a method whereby tissue coagulation and/or dissection can be effected, provides insight into the present invention. In electrosurgery, radiofrequency (RF) current is applied to tissue by an active electrode. In a bipolar system, the current is passed through tissue between two electrodes on the same surgical instrument, such as a forceps. In a monopolar system, a return-path (ground) electrode is affixed in intimate electrical contact with some part of the patient. Because of the importance of the ground electrode providing the lowest impedance conductive path for the electrical current, protection circuits monitoring the contact of the ground with the patient are often employed wherein an increase in ground electrode-skin impedance results in the instrument shutting down. Depending on treatment electrode shape, electrode position (contact or non-contact) with respect to the tissue surface, frequency and modulation of the radiofrequency, power of the RF and time for which it is applied to the tissue surface, peak-to-peak voltage of the radiofrequency, and tissue type, one may obtain desirable effects including cutting and coagulation of tissue. In a typical electrosurgical systems, radiofrequency frequencies of 300 kHz to 4 MHz are used since nerve and muscle stimulation cease at frequencies beyond 100 kHz.

For example, decreasing electrode size translates into increased current density in the tissue proximal to the electrode and so a more invasive tissue effect, such as dissection as compared to coagulation. Similarly, if the electrode is held close to the tissue but not in contact, then the area of radiofrequency-tissue interaction is smaller as compared to that when the electrode is in contact with the tissue, therefore, the effect on the tissue is more invasive. By changing the waveform of the applied radiofrequency from a continuous sinusoid to packets of higher peak voltage sinusoids separated by dead time (i.e. a duty cycle of 6%), then the tissue effect can be changed from dissection to coagulation. Increasing the voltage of the waveform increases the invasiveness of the tissue effect, and the longer the tissue is exposed to the radiofrequency, the greater the tissue effect. Finally, different tissues respond to radiofrequency differently because of their different electrical conductive properties, concentration of current carrying ions, and different thermal properties.

In the present invention, the following terms have the definitions set below.

As used herein, "dipole force" shall refer to a force which results when a molecule moves in order to achieve a more stable dipole state.

In one embodiment of the present invention, there is provided a method for enhancing continuous delivery of a pharmaceutical compound in a subject, comprising the steps of irradiating the subject with electromagnetic energy continuously; and applying the pharmaceutical compound to the subject. The pharmaceutical compound interacts with the electromagnetic energy. Examples of electromagnetic energy include radiofrequency, microwave and light. The pharmaceutical compound can be an antibiotics, cytokines, bone vascularization enhancers, anesthetic drugs, antineoplastic drugs, photodynamic therapeutical drugs, anti-infection drugs and anti-inflammatory drugs or any other drug that can interact with electromagnetic energy and be propelled through subject's barrier. A specific example of anesthetic drug is lidocaine.

In another embodiment of the present invention, there is provided a method for increasing diffusion rate of a substance in a medium, comprising the step of applying electromagnetic energy to said medium, wherein said electromagnetic energy generates propagating pressure wave upon said medium. The electromagnetic energy may be radiofrequency, microwave and light. The medium can be a liquid or semi-solid medium In still another embodiment of the present invention, there is provided a method for improving permeation rate of a molecule through a barrier, comprising the step of applying electromagnetic energy to the barrier, wherein the electromagnetic energy ablates or alters the structure of the barrier. The electromagnetic energy may be radiofrequency, microwave and light. The barrier can be biological and non-biological. Examples of biological barrier include skin, vaginal wall, uterine wall, intestinal wall, buccal wall, tongue, nasopharyngeal wall, anal wall, bladder wall, vascular vessel, lymphatic vessel and urethral vessel. Representative examples of non-biological barrier include a non-biological membrane, film and gel.

In yet another embodiment of the present invention, there is provided a method for creating pores in a barrier thereby improving permeation rate of a molecule through the barrier, comprising the step of applying electromagnetic energy with a probe to the barrier, wherein the probe conducts the electromagnetic energy. Specifically, the probe is made of a magnetic material, for example, silicon with a metallic conducting material.

In still yet another embodiment of the present invention, there is provided a method for enhancing continuous delivery of a pharmaceutical compound in a subject, comprising the steps of treating the subject to weaken the barrier function of its membrane first; irradiating the pre-treated subject with electromagnetic energy continuously; and applying the pharmaceutical compound to the subject. The electromagnetic energy may be radiofrequency, microwave and light. The subject can be pre-treated with electromagnetic energy, or using other membrane-weakening methods.

Further provided in the present invention is a system for enhancing continuous delivery of a pharmaceutical compound in a subject, comprising a means to generate electromagnetic energy; a means to deliver the electromagnetic energy to the subject continuously; and a means to administer the pharmaceutical compound to the subject. Preferably, the system further comprises a probe which is delivered to the subject at the same time as the electromagnetic energy. Specifically, the probe is made of a magnetic material, such as a metal or the probe is made of silicon with a metallic conducting material. The energy is selected from the group consisting of radiofrequency, microwave and light. A representative pharmaceutical compound is an anesthetic drug.

The following examples are given for the purpose of illustrating various embodiments of the invention and are not meant to limit the present invention in any fashion.

EXAMPLE 1

Pressure Waves for Driving Compounds through Skin or Membranes

Pressure waves created through the interaction of electromagnetic energy with tissue or non-biological matter may be used to drive molecules in a medium across tissue interfaces, between cellular junctions such as those found in membranes, between cells, or even through cellular membranes. The interaction of radiofrequency (RF) or microwave irradiation with tissue or another absorber can lead to the generation of propagating pressure waves, which were generated from a rapid volumetric change in the medium by heating, or by the generation of plasma. Propagating pressure waves are in the form of low pressure acoustic waves propagating at the speed of sound or high pressure shock waves propagating at supersonic speeds. These waves can also be a consequence of a generation of waves in anon-biological target which is in intimate acoustic contact with the biological media. Continuously pulsing electromagnetic energy delivered in discrete short duration pulses propagates the pressure waves which thereby physically move the molecules between cellular junctions or across membranes. The "pumping" effect may occur through the creation of increased pressure, including osmotic or atmospheric pressure. A separation results due to the differential resistance of the tissues or membranes relative to the fluid medium. The degree of pumping is related to the shape, duty cycle, and power of the driving radiofrequency.

Pumping may sometimes be inefficient if the energy is deposited directly on a tissue having a large surface area. To compensate for this inefficiency, a target which preferentially absorbs energy at these RF frequencies may be placed adjacent to the tissue. This target could effectively act as an antenna and may optionally be composed of metals or metal containing compounds.

The following experiment demonstrates this "pressure" principal: A Q-switched Nd:YAG laser producing radiant energy at 1064 nm is configured to produce 20 ns pulses with energies of 20 mJ at a pulse repetition rate of 10 Hz. The beam is focused to a circular spot with a diameter of 1 mm. A thin piece of black anodized aluminum is placed on the surface of a polyacrylamide gel, and a thin layer of aqueous trypan blue (4%) or other dye positioned between the aluminum and gel surface. The laser isoriented to irradiate the surface of the aluminum. The irradiation takes place for a period of 1 or more hours, after which time the aluminum is removed and the trypan blue remaining on the surface was removed with an absorptive towel. The gel is cut in cross section through the center of the two positions where the trypan blue is positioned. Upon transillumination with visible light, the trypan blue can be shown to have diffused further into the gel below the irradation site than where no laser irradiation took place.

A related experiment where the laser is oriented so the focusing lens is at the surface of the trypan blue may be used to demonstrate the result of electromagnetic energy induced pressure resulting from molecular absorption or scatter.

EXAMPLE 2
Pressure Waves for Altering the Barrier Function of Skin or Membranes The propagating pressure waves can be used to alter the skin or membrane, thereby reducing its barrier function. This barrier function alteration is transient and the integrity of the barrier function re-establishes soon after the RF energy ceases to impinge on the tissue. The degree to which the barrier function is reduced is dependent on the frequency and intensity of the radiofrequency radiation. The pharmaceutical compound to be applied to the tissue is preferentially in place during irradiation.

Continuous propagating pressure waves were used to make and keep the membrane permeable. These waves may or may not be shock-waves. Furthermore, the waves can be produced by devices that are not lasers. This method allows for continuous and controllable transmembrane drug delivery.

In this aspect of the invention, propagating pressure waves were created by rapid heating or plasma (creating subsonic or supersonic waves). Absorption of electromagnetic energy (EM) was performed by extracorporeal absorber (e.g. a piece of metal in intimate acoustic contact with the membrane of interest). More energetically efficient devices can be used. Optionally the devices can potentially be built into patches that use dry cells or solar cells as the source of power. Pumping is related to shape of initial EM pulse, duty cycle, and power of EM energy. The spectrum (wavelength and magnitude) of propagating waves is a function of the shape of the incident EM pulse. A variable duty cycle and power of the incident EM pulse provides a means with which the degree of drug delivery or biomolecule collection is controlled.

EXAMPLE 3
Incoherent Force

The incoherent interaction that can alter the momentum of an atom is also called the "scattering force" because it arises from direct scattering events. Every time an atom scatters a photon carrying momentum $p=h/\lambda$ (h is Planck's constant and $\lambda$ is the wavelength of light), the atom experiences a small change in velocity. In the case of incoherent scattering, two momentum impulses are delivered to the atom: one along the direction of the incident photon and the other opposite the direction of the scattered photon. Because the photons in rare media are not scattered into a preferred direction, the net average velocity change per scattered photon $\Delta v$ is opposite the direction of the incident photons with $\Delta v=p/M=h/\lambda M$, where M is the mass of the atom. Note that this force also provides a means to separate atomic or molecular species based on their mass, M.

The momentum imparted on the molecular target in an inelastic collision is equal to the ratio of the photon energy, U, divided by the speed of light, c. Given a critical amount of energy fluence (rate) in the electromagnetic energy continuous-wave beam or pulse, significant forces can be imparted on the molecular target, thereby inducing movement since force is equal to the time derivative of momentum.

This incoherent force could, for example, be used in the following way. The electromagnetic energy produced by a pulsed or continuous-wave Nd:YAG laser (1064 nm wavelength) could be used to irradiate a molecule (such as lidocaine-HCl) which does not significantly absorb energy having such wavelength. The molecule, if placed on the skin for example, would then scatter the electromagnetic energy in such a way that the net momentum imparted upon the molecule is in a direction away from the surface of the skin. Thus, the penetration of the drug into tissue would be enhanced as compared to passive diffusion.

The incoherent force on a molecule results when the molecule absorbs or scatters radiant energy. Such force is the momentum associated with photons, not a pressure wave pushing the molecules. Incoherent force is the most efficient when absorption takes place, although it's important that the molecule doing the absorbing does not undergo an irreversible change such as photolysis or chemical bond-breakage.

EXAMPLE 4
Coherent Force

The force arising from a coherent interaction with light is also called the dipole force. The laser field polarizes the atom, and the polarized atom experiences a force in the gradient of an electromagnetic field. The strong electric field of a laser beam can be used to induce a dipole moment in a process called optical trapping. As long as the frequency of the laser field is below the natural resonances of the particle being trapped (e.g. below the atomic transition of an atom or the absorption band of a polystyrene sphere), the dipole moment is in phase with the driving electrical field. Because the energy, W, of the induced dipole, p, in the laser field, E, is given by $W=-pE$; the particle achieves a lower energy state by moving into the high-intensity focal spot of the laser beam. There have been numerous reports of optical traps being used to manipulate particles, or even cells. These traps are used to move these tiny particles around under a microscope objective. Optical tweezers have also been described whereby a focal spot of a single beam optical trap is moved with mirrors or lenses. It has also been shown that other forms of electromagnetic energy may be used to form such "traps."

In the present invention, a "trap" is made by creating a non-uniform field of waves (e.g. photons, ultrasound, electric or magnetic). Due to the interaction of the molecule with the non-uniform field, there is a force imparted that tends to pull the molecule towards the most intense part of the field. Such trap is formed at the tissue interface where a desired molecular target is to be moved in a particular direction. In the case of drug delivery, the desired direction is into the tissues. Thus, the focal point of the trap is moved along a vector that penetrates the tissue of interest, while a formulation containing the drug is applied to the surface of the tissue. In the case of an optical trap, the focal point of a single beam or multiple beam trap would then be moved progressively into the tissue, which could occur cyclically so as to ensure the maximum pumping effect. Besides optical traps, other types of traps, such as magnetic, radiofrequency or microwave traps would also be useful.

The most intense part of the field (typically the focal point of some optic) was moved in a way such that the molecules are dragged into or out of the tissue. This method allows for continuous and controllable transmembrane drug delivery.

Radiofrequency or microwave radiant energy would be most suitable as the physical size of the volume whereby a driving force could be created is much larger than it is when light is used. Optical traps using light are microns in size, while traps using microwaves or RF could be centimeters in size. Furthermore, because microwaves and RF are not scattered in tissue as much as light, the former would be able to maintain their integrity to a greater depth in tissue than light.

EXAMPLE 5
Creation of Pores in Skin or Membranes

Small pores are made in the skin or membrane by applying the electromagnetic energy with needle-like probes. For example, a patch-like device with thousands of tiny, needle-like probes which conduct electromagnetic energy can deliver the energy to create pores. These probes can be made of silicon with a metallic conducting material.

The present invention considers the importance of specifically targeting the molecular species within the tissue of interest (i.e. not the applied drug) with the purpose of enhancing drug delivery or biomolecule collection. The alteration of the molecules, generally by inducing motion in the molecules and subsequently structures of which the molecules make up, and potentially altering intra- or inter-molecular bonds, is controllable and only occurs during application of the energy. For example, by targeting the lipid species in stratum corneum with radiant energy absorbed by the lipids, it is possible to reduce the barrier function of stratum corneum that results from these species and to effectively create "pores" in the skin thus providing channels through which drugs or biomolecules can permeate.

EXAMPLE 6
Ablation or Alteration of Membranes and Tissues

Radiofrequency or microwave energy is applied directly to the surface of the tissue, or to a target adjacent to the tissue, in such a way that the epithelial layers of the tissue are altered to make the layers "leaky" to substances such as pharmaceuticals. In the case of skin, the stratum corneum may be ablated through the application of electromagnetic energy to generate heat. Alternatively, shear forces may be created by targeting this energy on an absorber adjacent to the skin, which transfers energy to create stress waves that alter or ablate the stratum corneum. Specifically, radiofrequency which produces a desired rapid heating effect on stratum corneum results in an ablative event while minimizing coagulation. The removal of the stratum corneum in such way results in increased permeability of compounds across the compromised tissue interface. For example, application of 4% lidocaine to a section of skin with stratum corneum ablated by electromagnetic energy results in a rapid (minutes to onset) anesthesthetic effect.

Alternatively, delivery of electromagnetic energy at these wavelengths may be optimized by adjusting pulse duration, dwell time between pulses and power to result in a rapid, intermittent excitation of molecules in the tissues of interest. There is no net coagulation effect from heating, however, molecules are altered transiently to cause a transient change in membrane conformation that results in greater "leakiness" to substances such as pharmaceuticals. Electromagnetic energy with appropriate wavelengths and pulse mode characteristics were applied continuously so that the transient alterations in membrane conformation are maintained, thus creating a means for maintaining increased membrane permeability over time. This allows substances to be continually delivered over a desired period of time.

In the present invention, very small pores were created by using EM energy (such as RF waves) electronically coupled to electrically conducting needle-like probes (e.g. in the form of a patch), which is in contact with skin. These probes can be made, for example, of silicon and with micron sizes and can be made into an x-y array on a patch. Subsequent coating with an electrical conductor would be required. Depending on the nature of the energy applied, it would be possible to either alter or ablate the tissue. Finally, it is possible, using lithography, to create hollow needles whereby the drug or biomolecule could be delivered or collected through.

An electrosurgical unit, manufactured by Valley Labs, Inc (Colorado), was set to a continuous power of 2 Watts. A flat-tip applicator was attached to the unit. The grounding pad of the electrosurgical unit was fixed to the forearm of several human volunteers. The electrosurgical unit was initiated for a period of time estimated to be 300 milliseconds when the flat-tip of the applicator was place in delicate contact with the tissue approximately 10 cm away from the grounding pad. No sensation during treatment was apparent and no visible change in the treatment site was apparent. The site of treatment was marked with a pen and subsequently, 10% xylocaine was administered to the treated site and left on for a period of 5 minutes. Tests of the degree of anesthesia were done at the site by puncturing the skin with a 2.4 mm lancet. As compared to untreated control sites where xylocaine was place, the treated site exhibited more anesthesia.

EXAMPLE 7
Applying Pressure to Permeabilized Membranes for Molecular Delivery or Fluid Collection A "leaky" membrane or ablation site in skin is created by first applying electromagnetic energy, including light, microwave or radiofrequency. As a result, membrane or intramembrane structures are realigned to improve permeation. This step is followed by application of electromagnetic energy induced pressure to drive molecules across tissue interfaces and between cellular junctions at a greater rate. The laser energy may be delivered continuously or in discrete pulses to prevent closure of the pore. Optionally, a different wavelength laser may be used in tandem to pump molecules through the pore than what is used to create the pore. Alternatively, a single laser may be modulated so that pulse width and energy may vary over time to alternately create a pore through which the subsequent pulse drives the molecule.

Intact skin is treated such that the stratum corneum is compromised leading to a decreased resistance and increased permeability to molecules in general. This step is followed by application of electromagnetic energy-generated pressure wave to drive molecules across membranes and between cellular junctions at a greater rate.

Laser energy is directed through optical fibers or guided through a series of optics to generate pressure waves which come in contact with or create a gradient across the membrane surface. These pressure waves may be optionally used to create a pressure gradient across a liquid or semi-solid medium, thereby "pump" compounds through the medium. This technology may be used for delivering drugs across various biological membranes, such as buccal, uterine, intestinal, urethral, vaginal, bladder or ocular membranes. Pharmaceutical compounds may be delivered into cellular spaces beyond these membranes or into chambers encompassed by these membranes. Compromised or intact stratum corneum may also be breached by applying appropriate optical pressure.

EXAMPLE 8
Drug Formulations

Any alteration in a molecule, such as dimerization or the addition of a group, will change the absorption and scattering properties of the molecule. An increase in either will increase the efficiency of the dipole trap. For example, addition of magnetic species (ferro-, para- and diamagnetic) will enhance the effect of magnetic fields on the molecule. Alternatively, acoustical properties of molecules can be changed by addition of contrast enhancers such as galactose. The addition of this molecule would enhance the magnitude of the push. When using the coherent force to move molecules, it may be beneficial to alter the (drug) molecule by enhancing it's scattering cross section through the conjugation of a molecule to, for example, decrease the wavelength of resonance or decrease the natural lifetime.

Specific drug formulations were selected so that electromagnetic energy absorption is maximized relative to the surrounding medium. Many pharmaceutical or diagnostic compounds can be modified by the addition of energy absorbing groups to maximize the effects of the electromagnetic energy on a particular formulation relative to the surrounding medium or tissue. A new class of compounds may be defined by their unique permeability and migration characteristics in the presence of or following a treatment of electromagnetic energy. These molecules possess different characteristics by virtue of the addition of energy absorbing structures. As a result, the molecules are imparted momentum to move relative to the surrounding medium, or are altered due to the excitation of the molecules. For example, rapid heating of a molecule preferentially absorbing energy relative to its environment by radiofrequency or microwave energy could result in cleavage of a heat-sensitive linkage or activation of a specific activity. These compounds are designed to include both physiologically active groups and molecular groups that maximize the absorbance or reflectance of energy to achieve the desired effect. For example, an analogy is drawn to photodynamic therapy whereby molecules absorb photons and make interstate transition from ground to excited singlet state. By doing so, the molecules transfer energy to ground state oxygen, thus excite the ground state to an excited singlet state that is toxic.

Similarly, pharmaceutically active compounds may be modified by the addition of groups that readily form a dipole when exposed to appropriate electromagnetic energy, such as radiofrequencies or microwaves. The addition of such groups would result in enhanced ability to use optical trapping methods for the delivery of these types of compounds.

In general, any compound which may interact with electromagnetic energy in such a way that it is propelled through a medium may be used in the present invention. Thus, a means by which molecules may be propelled through a medium at differential rates relative to the medium and other molecules in the medium is defined. Also provided is a means by which molecules may be separated from one another based on their optical characteristics. The present invention is not limited to biomedical applications, as other separations of molecules may also be achieved by the methods described herein. Other examples include separating protein species in polyacrylamide gels, or separating oligonucleotides on microarray devices. The method disclosed herein also include using magnetic fields alone to propel molecules through a medium or tissue due to intrinsic magnetic properties or by the addition of magnetic groups, such as metals. Effects may be enhanced by synergism.

Any patents or publications mentioned in this specification are indicative of the levels of those skilled in the art to which the invention pertains. These patents and publications are herein incorporated by reference to the same extent as if each individual publication was specifically and individually indicated to be incorporated by reference.

One skilled in the art will readily appreciate that the present invention is well adapted to carry out the objects and obtain the ends and advantages mentioned, as well as those inherent therein. The present examples along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method for enhancing continuous delivery of a pharmaceutical compound in a subject, comprising the steps of:
   irradiating said subject with electromagnetic energy continuously; and
   applying said pharmaceutical compound to said subject.

2. The method of claim 1, wherein said electromagnetic energy is selected from the group consisting of radiofrequency, microwave and light.

3. The method of claim 1, wherein said pharmaceutical compound interacts with said electromagnetic energy.

4. The method of claim 1, wherein said pharmaceutical compound is selected from the group consisting of an antibiotics, cytokines, bone vascularization enhancers, anesthetic drugs, antineoplastic drugs, photodynamic therapeutical drugs, anti-infection drugs and anti-inflammatory drugs.

5. The method of claim 4, wherein said anesthetic drug is lidocaine.

6. A method for increasing diffusion rate of a substance in a medium, comprising the step of:
   applying electromagnetic energy to said medium, wherein said electromagnetic energy generates propagating pressure wave upon said medium.

7. The method of claim 6, wherein said electromagnetic energy is selected from the group consisting of radiofrequency, microwave and light.

8. The method of claim 6, wherein said medium is a liquid or semi-solid medium.

9. A method for improving permeation rate of a molecule through a barrier, comprising the step of:
   applying electromagnetic energy to said barrier, wherein said electromagnetic energy ablates or alters the structure of said barrier.

10. The method of claim 9, wherein said electromagnetic energy is selected from the group consisting of radiofrequency, microwave and light.

11. The method of claim 9, wherein said barrier is selected from the group consisting of biological and non-biological barrier.

12. The method of claim 11, wherein said biological barrier is selected from the group consisting of skin, vaginal wall, uterine wall, intestinal wall, buccal wall, tongue, nasopharyngeal wall, anal wall, bladder wall, vascular vessel, lymphatic vessel and urethral vessel.

13. The method of claim 11, wherein said non-biological barrier is selected from the group consisting of a non-biological membrane, film and gel.

14. A method for creating pores in a barrier thereby improving permeation rate of a molecule through said barrier, comprising the step of:
   applying electromagnetic energy with a probe to said barrier, wherein said probe conducts said electromagnetic energy.

15. The method of claim 14, wherein said probe is made of silicon with a metallic conducting material.

16. A method for enhancing continuous delivery of a pharmaceutical compound in a subject, comprising the steps of:

treating said subject to weaken the barrier function of its membrane;

irradiating the pre-treated subject with electromagnetic energy continuously; and applying said pharmaceutical compound to the subject.

17. The method of claim 16, wherein said electromagnetic energy is selected from the group consisting of radiofrequency, microwave and light.

18. The method of claim 16, wherein said pharmaceutical compound is an anesthetic drug.

19. A system for enhancing continuous delivery of a pharmaceutical compound in a subject, comprising:

a means to generate electromagnetic energy;

a means to deliver said electromagnetic energy to said subject continuously; and a means to administer said pharmaceutical compound to said subject.

20. The system of claim 19, further comprising a probe, wherein said probe is delivered to said subject together with said electromagnetic energy.

21. The system of claim 20, wherein said probe is a magnetic material.

22. The system of claim 21, wherein said probe is made of silicon with a metallic conducting material.

23. The system of claim 19, wherein said electromagnetic energy is selected from the group consisting of radiofrequency, microwave and light.

24. The system of claim 19, wherein said pharmaceutical compound is an anesthetic drug.

* * * * *